United States Patent
Benson et al.

(10) Patent No.: US 10,405,414 B2
(45) Date of Patent: Sep. 3, 2019

(54) LAMP BYPASS SWITCH

(71) Applicant: Amico Clinical Solutions Corporation, Richmond Hill (CA)

(72) Inventors: Wayne Benson, Newmarket (CA); Varun Chandan, Caledon (CA)

(73) Assignee: Amico Clinical Solutions Corporation, Richmond Hill (CA)

( * ) Notice: Subject to any disclaimer, the term of this patent is extended or adjusted under 35 U.S.C. 154(b) by 0 days.

(21) Appl. No.: 15/597,583

(22) Filed: May 17, 2017

(65) Prior Publication Data

US 2017/0251543 A1    Aug. 31, 2017

Related U.S. Application Data

(63) Continuation-in-part of application No. 15/013,423, filed on Feb. 2, 2016, now abandoned.

(60) Provisional application No. 62/110,880, filed on Feb. 2, 2015.

(51) Int. Cl.
| | |
|---|---|
| H02J 7/00 | (2006.01) |
| H05B 37/03 | (2006.01) |
| F21V 21/26 | (2006.01) |
| F21V 23/04 | (2006.01) |
| A61B 90/30 | (2016.01) |
| A61B 90/35 | (2016.01) |
| F21W 131/20 | (2006.01) |

(52) U.S. Cl.
CPC ............. *H05B 37/03* (2013.01); *A61B 90/30* (2016.02); *A61B 90/35* (2016.02); *F21V 21/26* (2013.01); *F21V 23/04* (2013.01); *F21W 2131/20* (2013.01)

(58) Field of Classification Search
CPC  H05B 33/14; H05B 37/0209; H05B 37/0236; H05B 37/036; H05B 39/044; H05B 3/34
USPC ......... 315/291, 294, 292, 312, 297, 152, 86, 315/112
See application file for complete search history.

(56) References Cited

U.S. PATENT DOCUMENTS

| | | | |
|---|---|---|---|
| 5,039,832 A * | 8/1991 | Polacek | H03K 17/18 200/317 |
| 6,034,581 A | 3/2000 | Dimarco et al. | |
| 7,218,056 B1 * | 5/2007 | Harwood | G08B 7/066 307/66 |
| 7,294,977 B1 | 11/2007 | Eusterbrock et al. | |
| 7,321,385 B2 | 1/2008 | Rus et al. | |
| 2003/0210559 A1 * | 11/2003 | Jesurun | F21V 21/403 362/572 |
| 2007/0030702 A1 * | 2/2007 | Held | F21V 23/04 362/647 |
| 2010/0328849 A1 | 12/2010 | Ewing et al. | |

(Continued)

OTHER PUBLICATIONS

U.S. Office Action, U.S. Appl. No. 15/013,423, dated Jul. 15, 2016.

(Continued)

*Primary Examiner* — Douglas W Owens
*Assistant Examiner* — Wei Chan
(74) *Attorney, Agent, or Firm* — Ridout & Maybee LLP

(57) ABSTRACT

Aspects of the present application relate to a bypass switch for a lamp, such as a surgical or diagnostic lamp. When activated, the bypass switch may act to allow electric power to bypass elements of a control board so that the electric power is provided to the plurality of lamp elements.

9 Claims, 4 Drawing Sheets

(56) References Cited

U.S. PATENT DOCUMENTS

| | | |
|---|---|---|
| 2011/0116288 A1 | 5/2011 | Sauter et al. |
| 2011/0133655 A1 | 6/2011 | Recker et al. |
| 2011/0187270 A1* | 8/2011 | Summerford ............. F21S 4/00 315/113 |
| 2013/0214609 A1* | 8/2013 | Carmen, Jr. ....... H05B 37/0227 307/104 |
| 2015/0035437 A1* | 2/2015 | Panopoulos ............ F21V 14/02 315/112 |
| 2016/0037602 A1 | 2/2016 | Nicholls |

OTHER PUBLICATIONS

U.S. Office Action, U.S. Appl. No. 15/013,423, dated Nov. 17, 2016.

* cited by examiner

LAMP BYPASS SWITCH

CROSS-REFERENCE TO RELATED APPLICATIONS

The present application is a continuation-in-part application of U.S. application Ser. No. 15/013,423, filed Feb. 2, 2016. Notably, U.S. application Ser. No. 15/013,423 claims priority to U.S. Provisional Patent Application No. 62/110,880, filed Feb. 2, 2015, the contents of which are hereby incorporated herein by reference.

FIELD

The present application relates generally to lamps and, more specifically, to a switch for bypassing lamp control electronics.

BACKGROUND

Control for lamps, such as those lamps used in surgical and diagnostic settings, may currently extend well beyond the on/off control of days gone by. Especially when a lamp is comprised of a plurality of dimmable lamp elements, control for a given lamp may involve turning on or off individual ones of the lamp elements and even controlling the amount of light generated at each lamp element. However, the main control boards that facilitate this degree of control are not immune to failure.

BRIEF DESCRIPTION OF THE DRAWINGS

Reference will now be made, by way of example, to the accompanying drawings which show example implementations; and in which.

DETAILED DESCRIPTION

Aspects of the present application relate to a bypass switch for a lamp, such as a surgical or diagnostic lamp. When activated, the bypass switch may act to allow electric power to bypass elements of the circuitry of a main control board so that the electric power is provided to the plurality of lamp elements.

According to an aspect of the present disclosure, there is provided a lamp assembly. The lamp assembly includes a plurality of light sources, a source of electrical power, a control board, a fuse board configured to provide, in accordance with control signals received from the control board, the electrical power, received from the source of electrical power, to the light sources and a bypass switch configured to, responsive to activation, transmit an override signal to the fuse board, wherein the fuse board is configured to, responsive to receipt of the override signal, provide the electrical power, received from the source of electrical power, to the light sources without regard to the control signals received from the control board.

Other aspects and features of the present disclosure will become apparent to those of ordinary skill in the art upon review of the following description of specific implementations of the disclosure in conjunction with the accompanying figures.

Figure 1:
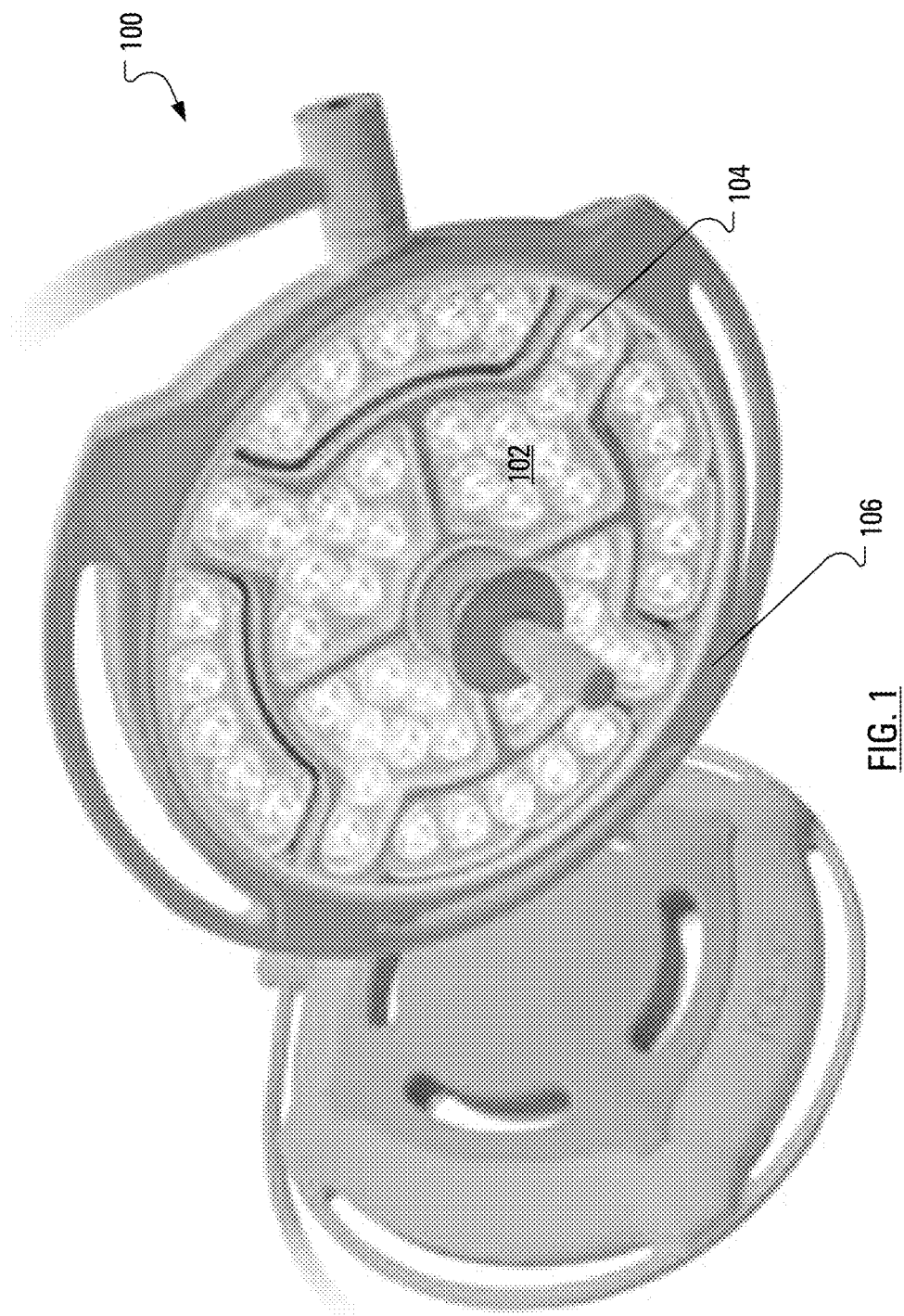
FIG. 1 illustrates a lamp.

FIG. 1 illustrates a lamp 100 having a plurality of lamp element assemblies 102. Mounted on each lamp element assembly 102 of the plurality of lamp element assemblies 102 is a plurality of lamp elements 104. The lamp element assemblies 102 may be mounted within a lamp head 106.

Figure 2:
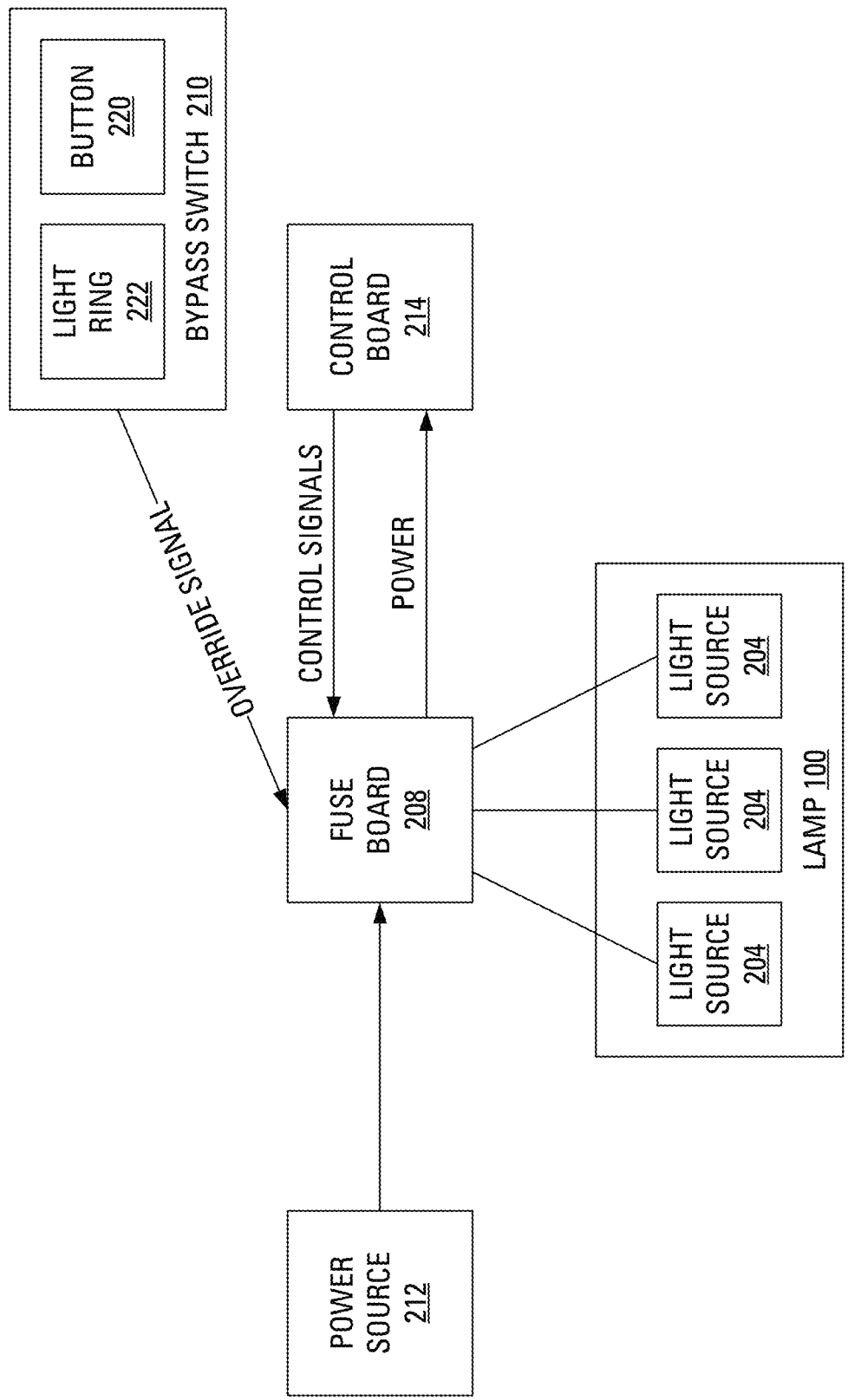
FIG. 2 illustrates, in block diagram form, the lamp of FIG. 1 and a plurality of control elements, including a fuse board, one of the control elements including a button, in accordance with aspects of the present application.

FIG. 2 illustrates, in block diagram form, the lamp 100 of FIG. 1 and a plurality of control elements. The lamp 100 includes a plurality of dimmable light sources 204. Each of the light sources 204 may be considered to be a component of a lamp element 104 of FIG. 1. The light sources 204 are configured to receive electrical power from a fuse board 208. The fuse board 208 may be communicatively connected to a control board 214. In particular, the fuse board 208 may provide power to the control board 214 and receive control signals from the control board 214.

The fuse board 208 is configured to receive electrical power from a power source 212.

Associated with, and communicatively connected to, the emergency bypass switch 210 are a button 220 and a light ring 222.

Figure 3:
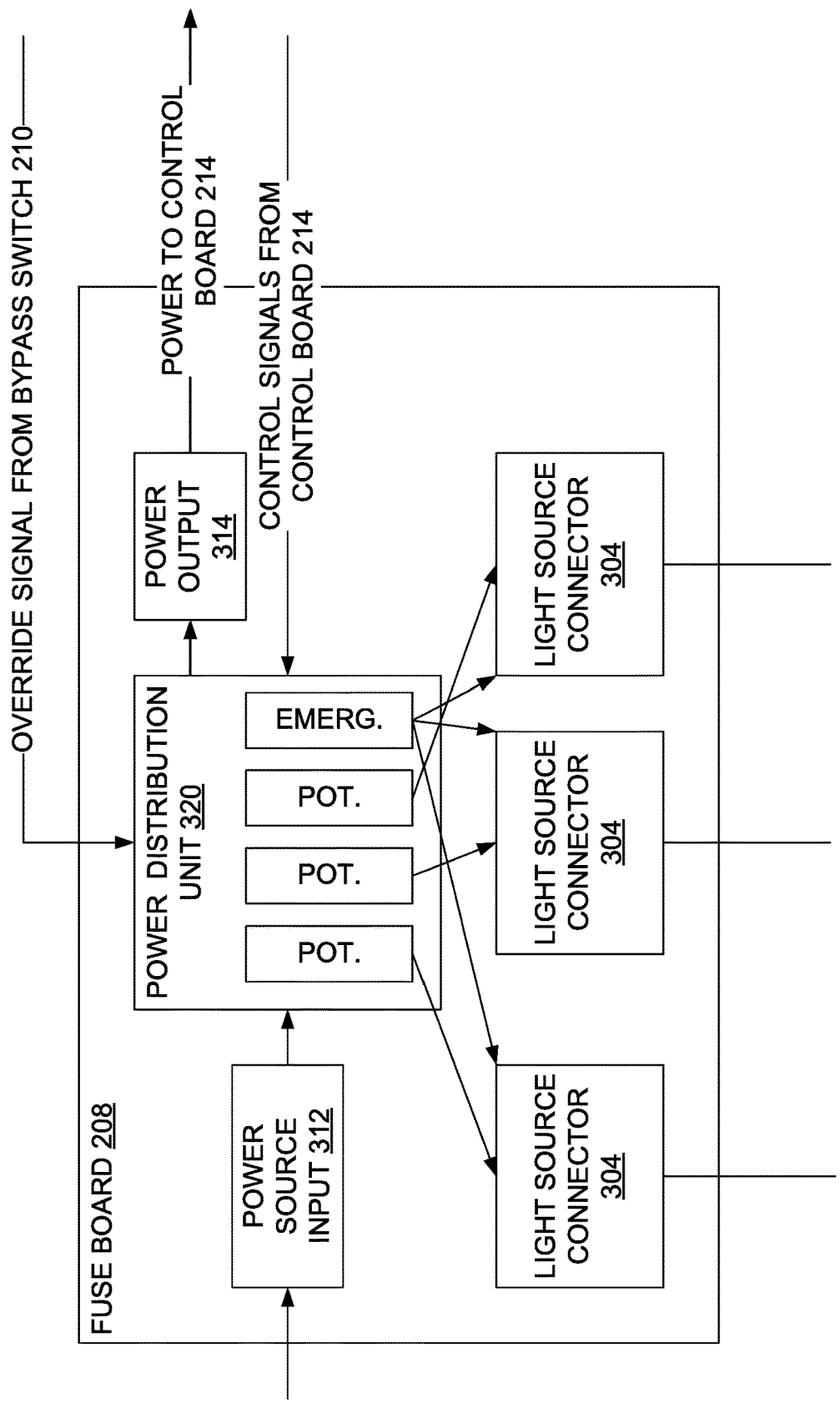
FIG. 3 illustrates, in block diagram form, the fuse board of FIG. 2, in accordance with aspects of the present application.

FIG. 3 illustrates, in further detail, the fuse board 208 of FIG. 2.

The fuse board 208 is equipped with typical pin-type connections to external components. For example, the fuse board includes a power source input 312 for receiving power from the power source 212. The control board 214 is arranged to receive some of the power received, at the fuse board 208 from the power source 212. Accordingly, the fuse board 208 includes a power output connector 314 to allow the fuse board 208 to provide power to the control board 214. The fuse board 208 also includes connectors 308 for connecting to the light sources 204.

A power distribution unit 320 acts to handle much of the tasks of the fuse board 208 and maintains connections to the power source input 312, the light source connectors 304 and the power output 314. Additionally, the power distribution unit 320 is adapted to receive control input from the control board 214 and to receive the override signal from the bypass switch 210.

The power distribution unit 320 may include P-Channel MOSFET transistors (not shown). The power distribution unit 320 may also include normal drive circuitry (not shown) and emergency drive circuitry (not shown). The normal drive circuitry may, for example, include a potentiometer associated with each of the light source connectors 304. The control signals from the control board 214 may be received by the potentiometers to adjust the power supplied to light sources 204 according to user settings. The emergency drive circuitry may be pre-configured with a particular power to provide to the light sources 204.

Figure 4:
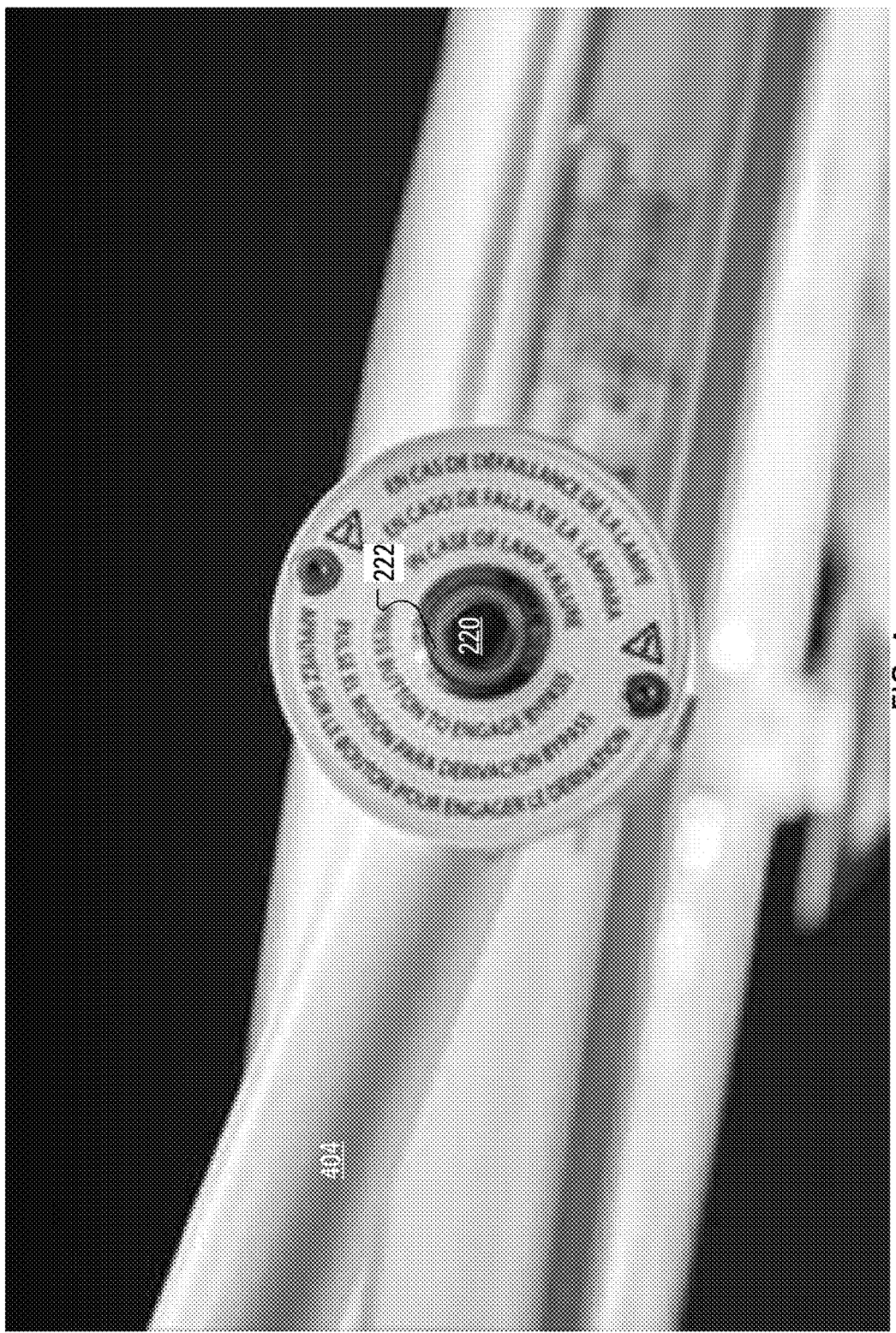
FIG. 4 illustrates the button of FIG. 2 on a swing arm, where the swing arm may be a support arm for the lamp of FIG. 1.

FIG. 4 illustrates the button 220 on a swing arm 404. The swing arm 404 may be, for example, a support arm for the lamp 100. The button is surrounded by the light ring 222.

In overview, aspects of the present application relate to the bypass switch 210 for the lamp 100, which may be a surgical or diagnostic lamp. The bypass switch 210 may be configured for use during emergencies, when the lamp 100 may be inoperable due a failure related to the control board 214.

In routine operation, the dimmable light sources 204 are configured to receive electrical power from the fuse board 208. A matter of which of the plurality of light sources 204 receives electrical power and the quantity of power may be determined, at the fuse board 208, based on control signals received, at the fuse board 208, from the control panel 214. The control panel 214 may generate such control signals, based upon manipulation by a user of the lamp 100, and transmit such control signals to the fuse board 208. More particularly, the control signals from the control panel 214 may be implemented as pulse width modulated signals, with the width of the pulse being representative of a degree to which individual ones of the dimmable light sources 204 are to be dimmed. Indeed, the degree of dimming may range from 0% to 100%. Elements (not shown) of the circuitry of the fuse board 208 control the degree of dimming of the individual ones of the dimmable light sources 204 based upon the control signals received from the control panel 214.

As stated hereinbefore, it is generally unlikely that the control board 214 is immune to failure. Failure of the control board 214 may lead to apparent inoperability of the lamp 100.

Upon detecting apparent inoperability of the lamp 100, a user of the lamp 100 may activate the bypass switch 210. The user of the lamp 100 may, for example, activate the bypass switch 210 by pressing the button 220 (see FIG. 4) on the swing arm 404.

The bypass switch 210, responsive to having been activated, transmits an override signal to the fuse board 208. At the fuse board 208, the effect of receipt of the override signal from the bypass switch is to allow the electrical power provided by the power source 212 to bypass the elements of the circuitry of the fuse board 208 that control the degree of dimming of the individual ones of the dimmable light sources 204 such that the electrical power proceeds to the plurality of light sources 204 with, for example, 0% dimming.

In normal operation, the transistors of the power distribution unit 320 are in the conducting state. In the conducting state, the transistors allow the potentiometer-controlled power to pass through to the light source connectors 304 and then out to respective light sources 204.

Responsive to the override signal from the bypass switch 210, emergency operation is enabled. The override signals is received at the gate of each transistor. Responsive to the override signal, each transistor turns off. In the off state, the transistors do not allow the potentiometer-controlled power to pass through to the light source connectors 304. Instead, only the signal from the emergency drive circuitry is allowed to pass through to the light source connectors 304 and then out to respective light sources 204.

As a result of not passing through elements of the circuitry of the fuse board 208, the electrical power provided to the plurality of light sources 204 lacks any attenuation (dimming) or individual light source control. As such, responsive to activation of the bypass switch 210, all of the light sources 204 may be configured to turn on and glow at full power.

Further responsive to activation of the bypass switch 210, the light ring 222 may be illuminated, thereby providing an indication that the bypass switch 210 has been activated.

When the emergency function is subsequently disabled through use of the button 220, the override signal to the gate of each transistor is removed and, responsively, the transistors return to the conducting state, thereby allowing the potentiometer-controlled power to pass through to the light source connectors 304 and then out to respective light sources 204.

Accidental activation of the bypass switch 210 may not be possible to avoid. However, through the illumination of the light ring 222, a user can readily observe whether the bypass switch 210 has been activated. Such an observation may serve as a clue as to why the lamp 100 is not reacting appropriately to user attempts at control via the control board 214.

Conveniently, when mounted on the swing arm 404, the bypass switch 210 is easily accessible. Other easily accessible locations are also contemplated, including on the lamp head 106 or any other connecting components.

The above-described implementations of the present application are intended to be examples only. Alterations, modifications and variations may be effected to the particular implementations by those skilled in the art without departing from the scope of the application, which is defined by the claims appended hereto.

What is claimed is:

1. A lamp assembly comprising:
    a plurality of light sources;
    a source of electrical power;
    a source of control signals;
    a control element including an normal drive circuitry and an emergency drive circuitry, the normal drive circuitry configured to provide, in accordance with first control signals received from the source of control signals, the electrical power, received from the source of electrical power, to the light sources via light source connectors, the normal drive circuitry including a potentiometer associated with each of the light source connectors; and
    a bypass switch configured to, responsive to activation, transmit an override signal to the control element;
    wherein the control element is configured to:
    receive, from the bypass switch, the override signal;
    receive, from the source of control signals, second control signals; and
    receive, from the source of electrical power, further electrical power; and,
    wherein the emergency drive circuitry is configured to, responsive to receiving the override signal, provide the further electrical power to the light sources via the light source connectors without regard to the second control signals.

2. The lamp assembly of claim 1 wherein the source of control signals is configured to:
    generate, based upon user manipulation, the first control signals; and
    transmit, to the control element, the first control signals.

3. The lamp assembly of claim 1 wherein the first control signals comprise pulse width modulation signals.

4. The lamp assembly of claim 1 further comprising a light ring wherein the bypass switch is configured to, responsive to activation, provide electrical power to the light ring.

5. The lamp assembly of claim 1 wherein the bypass switch further comprises a button for selective activation of the bypass switch.

6. The lamp assembly of claim 1 further comprising a lamp head, wherein the light sources are mounted within the lamp head.

7. The lamp assembly of claim 6 further comprising a swing arm configured to support the lamp head.

8. The lamp assembly of claim 7 wherein the button is mounted to the swing arm.

9. The lamp assembly of claim 8 wherein a light ring surrounds the button.

* * * * *